United States Patent
Sosnytskyy et al.

(10) Patent No.: US 9,804,125 B2
(45) Date of Patent: Oct. 31, 2017

(54) DEVICE FOR COMPENSATING ELECTROMAGNETIC INTERFERENCES DURING BIOMAGNETIC MEASUREMENTS

(76) Inventors: Volodymyr Mykolaiovych Sosnytskyy, Kiev (UA); Yurii Dmytrovych Minov, Kiev (UA); Mykola Mykolaiovych Budnyk, Kiev (UA)

(*) Notice: Subject to any disclaimer, the term of this patent is extended or adjusted under 35 U.S.C. 154(b) by 473 days.

(21) Appl. No.: 14/375,480

(22) PCT Filed: May 17, 2012

(86) PCT No.: PCT/UA2012/000049
§ 371 (c)(1),
(2), (4) Date: Jul. 30, 2014

(87) PCT Pub. No.: WO2013/115749
PCT Pub. Date: Aug. 8, 2013

(65) Prior Publication Data
US 2015/0008909 A1 Jan. 8, 2015

(30) Foreign Application Priority Data
Feb. 2, 2012 (UA) .................. 201201075

(51) Int. Cl.
*G01N 27/72* (2006.01)
*G01R 1/18* (2006.01)
(Continued)

(52) U.S. Cl.
CPC ............ *G01N 27/72* (2013.01); *G01R 1/18* (2013.01); *G01R 33/0076* (2013.01); *G01R 33/025* (2013.01); *G01R 33/1269* (2013.01)

(58) Field of Classification Search
CPC .......... G01N 27/72; G01R 1/18; G01R 33/00; G01R 33/035; G01R 33/025; G01R 33/022; G01C 17/00
(Continued)

(56) References Cited

U.S. PATENT DOCUMENTS 3,311,821 A   3/1967   Brunel
3,976,938 A   8/1976   Hesterman
(Continued)

FOREIGN PATENT DOCUMENTS

DE   320708 A1   9/1983
EP   0691547 A1  1/1996
(Continued)

OTHER PUBLICATIONS

Matlashov, N., et al., "Electronic Noise Suppression in Multichannel Neuromagnetic System", Advances in Biomagnetism, Eds., J. Williamsson et al., Plenum Press, pp. 725-728, 1989.
(Continued)

*Primary Examiner* — Jermele M Hollington
*Assistant Examiner* — Zannatul Ferdous
(74) *Attorney, Agent, or Firm* — Cozen O'Connor

(57) ABSTRACT

Invention, relates to the field of supersensitive biomagnetometry under presence of external electromagnetic interferences. In order to perform passive compensation of said interferences, design of device at the magnetometer input is proposed, comprising compensation elements and means for their moving including shifting, holding, and fixation units. In the basic embodiment, three short-closed wire contours are used which are orthogonally placed in space and independently moved up-down relative to the magnetometer or its input antenna. Contours are fixed in positions where minimum of external interference amplitude is achieved according to given field projection. Variants are proposed with cooling of meter and/or contours, location of contours inside the cryostat and their manufacturing from superconductors.

3 Claims, 3 Drawing Sheets

(51) Int. Cl.
*G01R 33/00* (2006.01)
*G01R 33/025* (2006.01)
*G01R 33/12* (2006.01)

(58) Field of Classification Search
USPC ........................................................ 324/225
See application file for complete search history.

(56) References Cited

U.S. PATENT DOCUMENTS

| | | | | |
|---|---|---|---|---|
| 4,889,124 | A | * | 12/1989 | Schneider ............... G01R 33/00 600/409 |
| 5,113,136 | A | | 5/1992 | Hayashi et al. |
| 5,122,744 | A | | 6/1992 | Koch |
| 5,152,288 | A | | 10/1992 | Hoenig et al. |
| 5,844,996 | A | | 12/1998 | Enzmann et al. |
| 6,462,540 | B1 | * | 10/2002 | Kandori ............... G01R 33/025 324/225 |
| 6,538,436 | B1 | * | 3/2003 | Simola .................. G01D 3/032 324/225 |
| 7,091,717 | B2 | | 8/2006 | Lee et al. |
| 7,656,154 | B2 | | 2/2010 | Kawabata et al. |
| 2004/0106863 | A1 | | 6/2004 | Seki |
| 2005/0088174 | A1 | | 4/2005 | Lee et al. |
| 2007/0120563 | A1 | | 5/2007 | Kawabata et al. |
| 2009/0143665 | A1 | | 6/2009 | Seki |

FOREIGN PATENT DOCUMENTS

| | | |
|---|---|---|
| FR | 2512965 A1 | 3/1983 |
| JP | 63174077 U | 11/1988 |
| JP | 2009125396 A | 6/2009 |

OTHER PUBLICATIONS

European Search Report issued Dec. 17, 2015 in corresponding European Patent Application No. 12867179.
Traslshawala N et al. "Reduction of ambient magnetic field noise for high-Tc SQUID applications". IEEE Transactions on Applied Superconductivity, IEEE Service Center, Los Alamitos, CA , US, vol. 7, No. 2, Jun. 1, 1997 (Jun. 1, 1997), pp. 2890-2893, XP011501061, ISSN: 1051-8223, DOI 10.1109/77.62189.
Wordenweber R et al. "Reduction of low-frequency noise in high-Tc SQUIDS by artificial defects", Physica C, North-Holland Publishing, Amsterdam, NL, vol. 366, No. 2, Jan. 1, 2002 (Jan. 1, 2002), pp. 135-146, XP0004329073, ISSN:0921-4534, DOI 10.1016/S0921-4534 (01) 00837-1.

* cited by examiner

DEVICE FOR COMPENSATING ELECTROMAGNETIC INTERFERENCES DURING BIOMAGNETIC MEASUREMENTS

FIELD OF INVENTION

The invention relates to the technical field of protection of high-sensitive measuring equipment against external interferences and could be used for protection against electromagnetic noises of systems, like magnetocardiographic complexes operated at unshielded premises.

PRIOR STATE-OF-ART

As the sensors in biomagnetic systems there are highly sensitive magnetometers used, such as superconductive quantum interference detectors (SQUIDs), optically pumping magnetometers or magnetoresistive sensors. These magnetometers are characterized by high magnetic field resolution in the range of pico-femto Tesla. At the same time useful magnetic signal spectrum of biological objects (for example, of the human heart) is concentrated in low-frequency range 0.1-100 Hz. Presence of industrial noises (radio-stations, mobile communications, electrostatic discharges and other sources of electromagnetic fields and waves) can disturb operation stability of these measuring instruments. The interference level, under which normal performance of magnetometers is still survived, typically should not exceed 0.1 nT.

High level of urban industrial noises requires application of additional passive and active protection of the measurement zone against magnetic interferences. Herewith maximum induction value of biomagnetic fields, such as magnetic field (MF) of human heart doesn't exceed 50 pT, so for reliable registration and recognition of so weak signals, there are special hardware and software tools should be used to reduce external MF of interferences in the measurement area by several orders of magnitude. Threat patient resides in the natural magnetic background, i.e. in MF of Earth, which is equal to approximately 50 µT.

There are following protective methods known against magnetic interferences:

1) Magnetically shielded rooms (MSR). Up to date, in order to ensure efficiency of biomagnetic systems there are passive electromagnetic screens widely used in the form of shielded rooms, which could cost several times higher compared to the cost of the measuring instruments themselves. Necessity to use MSR for biomagnetic measurements have been grounded in the U.S. Pat. No. 5,152,288 [A61B 5/04, A61B 5/05, G01 R33/00, G01R33/035, Apparatus and method for measuring weak, location-dependent and time-dependent magnetic fields, Hoening E., Reichenberger H., Schneider S., 1992]. However MSR—is expensive and technically complicated product, so only major research centers could afford to use it.

In addition, weakening degree of magnetic interference is insufficient in the case of sources that are close enough and create non-uniform MF in the measurement area. To reduce magnetic interference of this kind there several technical solutions have been developed, based on the principle of active noise reduction, which is widely used in other branches of engineering, for example U.S. Pat. No. 5,844, 996 [A61F 011/06, D. Enzmann, M. F. Anthony et al. Active electronic noise suppression system and method for reducing snoring noise, 1998].

2) Active noise compensation by means of induction coils. This method is based on the idea of using negative feedback (NFB): magnetic obstacle measured by reference sensor is used to generate MF with amplitude equal to the obstacle's one, but in the opposite direction. This MF is further used for subtraction (compensation) of the noise component of the measured signal.

For example, in biomagnetic measurements obstacle signal after amplification is transmitted as a current to the system of induction coils to create in the measurements zone MF opposite to the field of magnetic interference. Dimensions of the coils system are determined by the degree of MF homogeneity inside the system and the size of biological object. Idea of such compensation system is described in details in patents:

a) U.S. Pat. No. 3,311,821, G01C 17/38; G01R 33/025; G01C 17/00; G01R 33/025, J. J. A. Brunel, Apparatus for automatically compensating the output of a magnetic field sensing device for the effects of interfering magnetic fields, Mar. 28, 1967, b) U.S. Pat. No. 5,122,744, G01R 33/022; G01R 33/025, Koch, Roger H. (Amawalk, N.Y.); Gradiometer having a magnetometer which cancels background magnetic field from other magnetometers, Oct. 9, 1990.

3) Electronic noise suppression systems. The most widely used in biomagnetic measuring systems among known solutions there are so-called Electronic Noise Suppression System (ENSS) [see, for example, A. N. Matlashov et. al. In *Advances in Biomagnetism*, Eds. S. J. Williamson, M. Hoke, G. Stroink, and M. Kotani, Plenum Press, New York and London, pp. 725-728, 1989].

ENSS includes several magnetometers with rather low sensitivity (reference channels) with separate electronics, placed among gradiometer (signal) channels. Reference channels use magnetometers with lower sensitivity than ones in signal channels. Typically, reference channels record MF of interferences in 3 orthogonal projections and form a reference vector magnetometer (RVM). Output signals of RVM are inverted, scaled and mixed with outputs of signal channels. For example, if interference X-signal at the RVM output is higher (lower) than the interference X-signal at the output of signal channel, RVM signal is amplified (attenuated) and subtracted from the signal at the output of signal channel.

In this regard, there is well-grounded patent-analogue known U.S. Pat. No. 5,113,136 [Gradiometer apparatus with compensation coils for measuring magnetic fields, G01R 33/022, G01R 33/025, G01R 33/035, H. Hayashi, Yu. Igarashi, T. Hayashi et al, 1992, Fujitsu Ltd]. Invention discloses 17 implementation's of ENSS systems and covers virtually all possible solutions in magnetometry. In these solutions metering device contains RVM and multi-channel magnetometer, where MVR is used to record MF of interferences, which are then subtracted at the outputs of signal channels or at their inputs using NFB loops, with signals from MVR. Thus two of these ENSS options protected by patent claims 16 and 19, implement compensation at the input of signal channel with SQUID-magnetometer.

Advantage of the device according to U.S. Pat. No. 5,113,136 is that it intended just for biomagnetic measurements of MF from human body. As a drawback it should be noted that MVR also use SQUID-magnetometer, which increases cost and complicates biomagnetic measurement device.

Therefore recently proposed option of ENSS system according to U.S. Pat. No. 7,091,717 [SQUID sensor using auxiliary sensor, G01R 33/25, G01R 33/35, Seung Min Lee, Heon Joo Lee, Byung Du Oh, 2006, LG Electronics Inc.] uses referent magnetometer, NFB and compensation at the input of the signal SQUID-channel. Advantage of this solution is that in signal channel SQUID could be used manufactured from high-temperature superconductors, i.e. of nitrogen cooling level. Disadvantage is common to all active compensation systems—reference magnetometer and NFB are required.

However, the principal advantage of this solution is that the referent magnetometer could be implemented without SQUID, i.e. non-superconductive, and even without cooling. Sense of this change is that it does not require high resolution at strong magnetic interference level. This makes active compensation system much cheaper and simpler, so ENSS system offered in U.S. Pat. No. 7,091,717 was chosen as the prototype.

Developing idea of the prototype, could the signal channel be implemented without SQUID magnetometers? Current technology level evidences that such metering devices are based on magnetometers with optical pumping, see, e.g., U.S. Pat. No. 7,656,154 [Magnetic field measurement system and optical pumping magnetometer, G01R 33/035, G01V 3/00, G01R 33/02, R. Kawabata, A. Kandori, 2010, Hitachi High-Tech Corp.]. However, another disadvantage is also active compensation with induction Helmholtz coils; which requires reference magnetometer, which is similar to selected prototype, does not require cooling or superconductivity.

Thus, active noise compensation system, have several significant drawbacks caused by following factors:

1) external interferences could greatly exceed the useful signals, which places high demands on dynamic range of electronic feedback chains and can limit their functionality;

2) external interferences could be of rather high frequency, in this case compensation efficiency depends on performance rate of the electronic feedback compensators;

3) such compensation systems include additional electronic circuit with power supplies and controls, leading to increased overall cost of the metering device for biomagnetic signals and increased complexity of its adjustment.

SUMMARY OF THE INVENTION

The essence of proposed technical solution is following: instead of using reference magnetometers to register interference MF in three orthogonal directions X, Y, Z, proposed device use at least three rings of conductive materials (including superconductors), which are also orthogonally and close to the input antenna of biomagnetic metering device.

The novelty of proposed invention is in elimination of the drawbacks and limitations, specific to the prototype device, using relatively simple technical solutions:

1) offer device for compensation of magnetic interference, which does not contain active electronic feedback circuits.

2) proposed device has no restrictions on performance rate and dynamic range.

Invention is based on the task of improving design of the device for passive compensation of electromagnetic interferences in measurement of biomagnetic signals at a high level of external electromagnetic interference and lack of magnetic and/or electromagnetic shielding or active noise compensation, in order of its simplification and cheapening, implementation of regulated compensation for electromagnetic interference without necessity of device cooling to cryogenic temperatures, as well as using other types of biomagnetic metering devices instead of superconducting SQUID-magnetometers.

Assigned target is achieved by:
implementation of the device with at least one compensation element and relocation means of said element(s);
implementation of compensation elements in the form of short-circuited contours of arbitrary shape;
manufacturing of compensation elements from materials with high electrical conductivity (copper, aluminum, etc.);
manufacturing of compensation elements so that they have no galvanic coupling, but only inductive coupling with metering device;
allocation of compensation elements in the space so that each projection of a field or field gradient corresponds to at least one element;
implementation of relocation means in the fastening, displacement and fixing of compensation elements
implementation of relocation means for repeated displacement and fixation of compensation elements for changing of noise conditions at the location place of metering device;
implementation of the relocation means for independent movement of individual compensation elements;
implementation of fixation means for holding of compensation elements in positions with minimum noise amplitude at the input of metering device;
cooling of the metering device, for example, using cryogenic liquids or any other means, and placing it inside the cooler, and placing of compensating elements outside the cooler, such as cryostat or other instrument;
placing of at least one compensation element inside the cooler of metering device, for example, cryostat or other instrument;
manufacturing of at least one compensation element from superconducting materials.

The technical result is that a small number of passive elements in design of the proposed device provide its:
1) high efficiency;
2) cheapness;
3) alignment simplicity;
4) applicability to different types of biomagnetic measurement devices such as SQUID-magnetometers, magnetometers with optical pumping, based on magneto-resistive or other sensors.

DESCRIPTION OF THE PREFERRED EMBODIMENTS

The principle of passive compensation is following: electromagnetic or variable magnetic interference due to the phenomenon of electromagnetic induction generates eddy currents in the compensation element. These currents generate MF around this element, with direction opposite to the interference MF direction. Compensatory MF, which is the MFs vector sum of all 3 elements, enters the metering input, where it is added to the MF of interference. Amplitude and direction of the total compensation MP vector varies depending on position of the compensation elements relative to the metering device.

Figure 1:
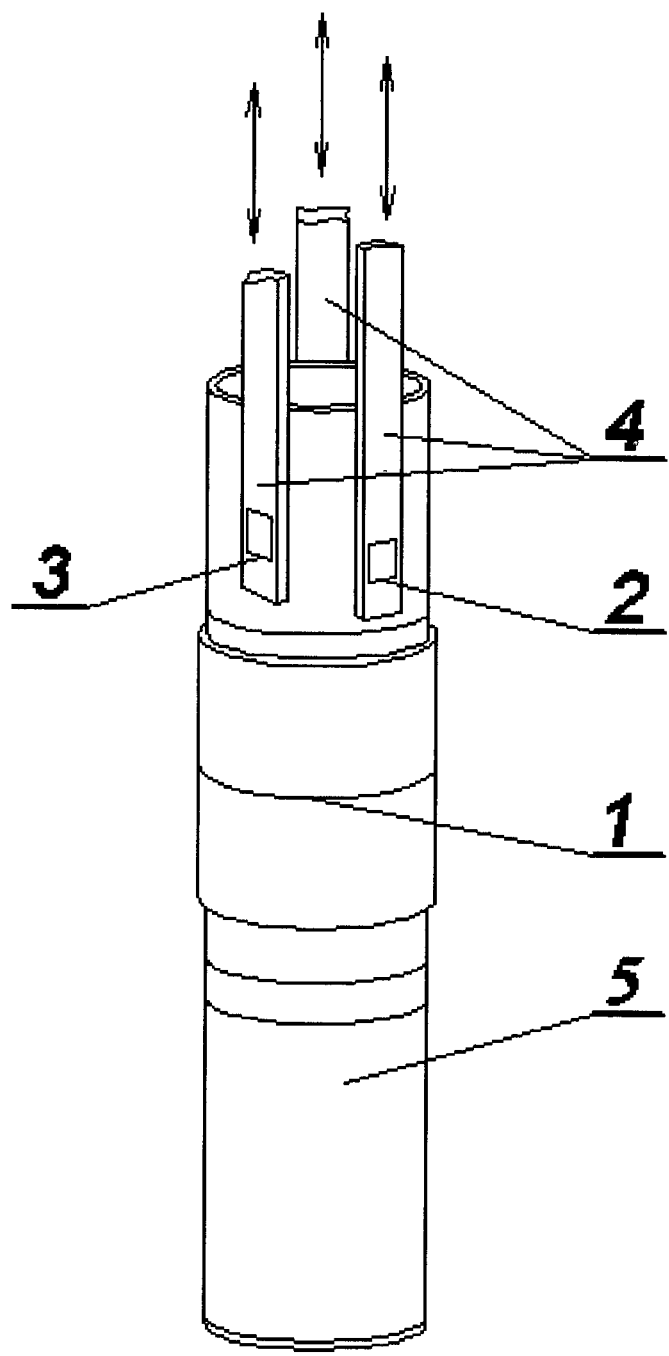
FIG. 1—Mutual arrangement of compensation rings for weakening of electromagnetic interference and biomagnetometer device: 1, 2, and 3 are ring to interference reduction along axis, Z, X, and Y, respectively, 4 is means for shifting of compensation rings, 5 is measuring device.

Relative position scheme of 3 short-circuited rings and measuring device for biomagnetic fields is shown in FIG. 1, which illustrates the principle of the invention. Compensation rings 1-3 are arranged in 3 mutually orthogonal planes, which make it possible to compensate magnetic interference independently of its direction. All rings are located directly near the metering device 5 in order to provide penetration of induced MF almost without weakening inside the metering device or inside its sensor or input antenna, if any.

In basic implementation of the compensation procedure elements are alternatively shifted up and down to control the level of interference on the meter output in absence of valid signal. At a certain position of each of 3 elements compensation field becomes approximately equal in amplitude and opposite in direction to the MF of interference. As a result, the amplitude of interference MF at the measuring device input and signal amplitude at its output would reach a minimum.

According to the basic implementation device also includes a separate mechanisms 4 (see. FIG. 1) for independent movement of each compensation ring relative to the metering device. The mechanisms consist of fastening elements, up and down shift elements and elements for fixing of the compensation rings in positions that provide minimum MF amplitude of the interference at the metering input. Parts of the mechanism provide frequent adjustment and fixing of rings according to changes of noise conditions in the measuring area.

Figure 2:
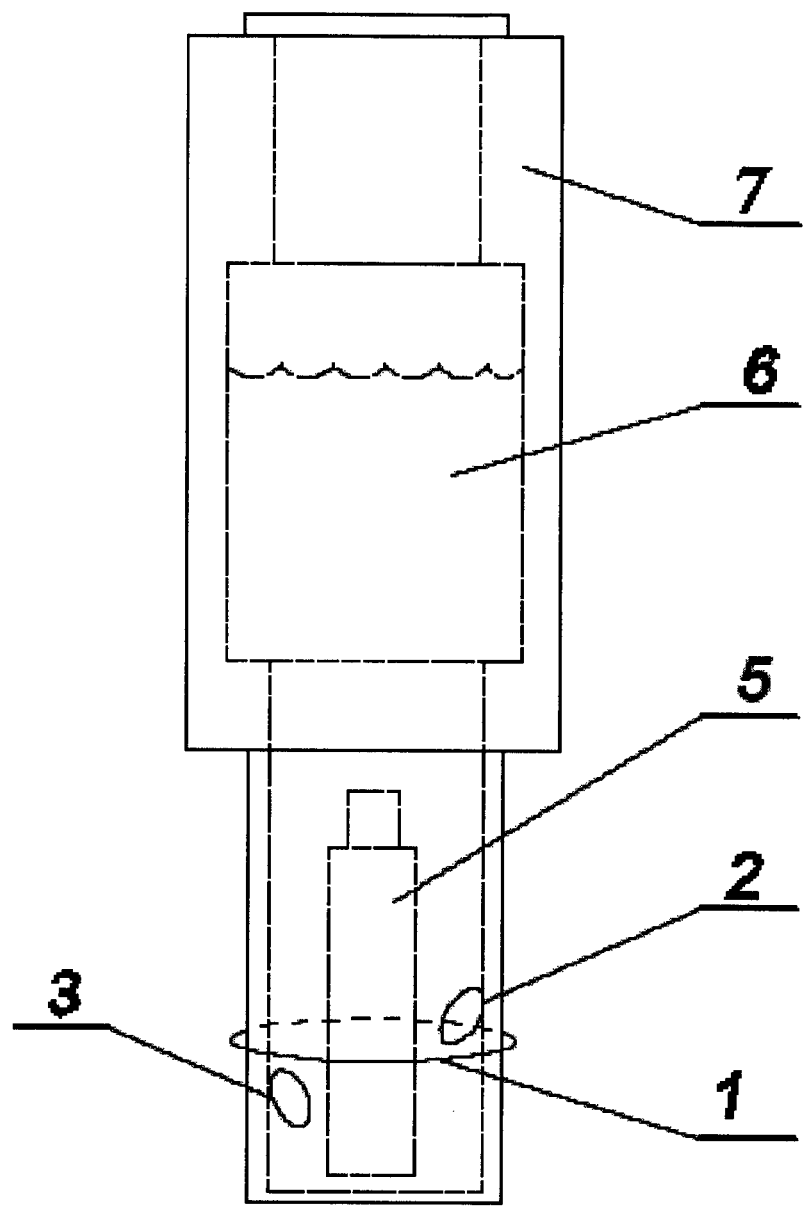
FIG. 2—Arrangement of compensating rings and cooled metering device: 1-3 and 5 are the same to FIG. 1, 6 is cryogenic liquid, 7 is magneto-transparent cryostat.

In another implementation of the device (see FIG. 2) is used to compensate interference MF at the input of highly sensitive cryogenic meter 5, which is cooled to reduce its own noise. In order to do this meter is placed in a cryostat 7, which is filled with cryogenic liquids 6, such as liquefied helium or nitrogen. Cryostat 7 for biomagnetic measuring device is made permeable to low-frequency MF—magnetotransparent therefore manufactured of dielectrics, such as non-magnetic fiberglass.

Thereat compensation rings 1-3 are fixed at cryostat surface or close to it, ensuring their temperature equal to ambient temperature, i.e. room temperature. According to the invention all compensation rings have only inductive coupling with the metering antenna when under the influence of induced currents MF enters the metering device, which compensates the interference MF.

Figure 3:
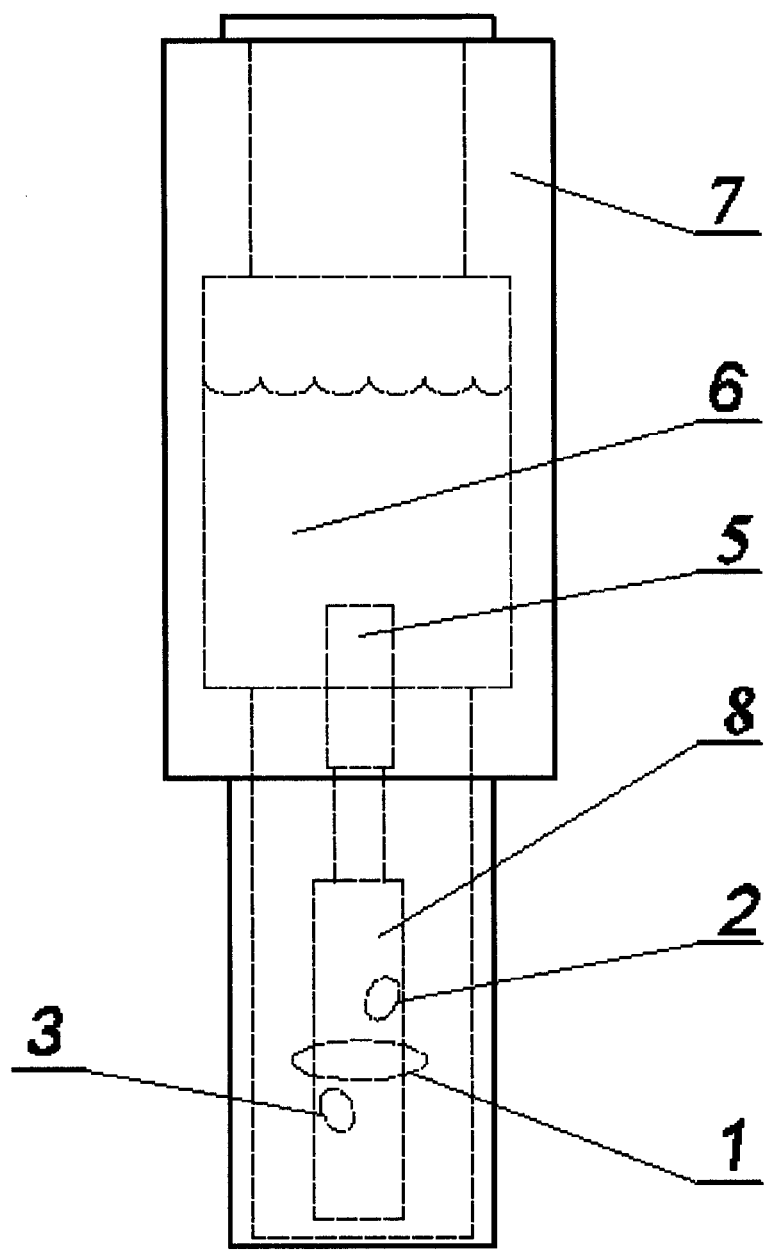
FIG. 3—Arrangement of cooled compensation elements and cryogenic measuring device of biomagnetic signals: 1-3 and 5-7 are the same to FIG. 2, 8 is superconducting antenna.

In yet another implementation device is implemented so that at least one of the compensation rings 1-3 is placed inside the cooler of the meter that provides closeness of its temperature to the temperature of the meter or refrigerant. FIG. 3 represents the version with cryogenic meter, for example, SQUID magnetometer, 5, and all rings 1-3 are placed inside the cryostat near the input metering antenna 8. Advantage of this option is possibility to increase current in the rings due to a decrease in their resistance by cooling, and to increase the amplitude of compensatory MF by reducing distance to the metering antenna. Drawback—it's much harder to implement moving and fixing of rings inside the cryostat.

In yet another implementation at least one compensation element is manufactured of superconductive materials. Then the resistance of the ring may decrease to zero if the temperature inside the cryostat is lower than the superconductor's transition temperature to the superconductive state. Advantage of this option—no damping of induced currents with frequency increasing, which allows compensation for a wide frequency range. Limitation of this implementation—it makes sense only for cryogenic metering device, placed in a cryostat.

In another implementation there is used at least one additional compensation element that is placed in space so that it matches a particular spatial component of the field gradient. Number of additional elements depends on the number of said components, which are registered by the metering device, or the number of interference gradient components that should be compensated.

In another implementation device is used to compensate interference MF at the input of multi-channel meter. Thereat optimum position of the compensation elements is determined by the minimum amplitude of interference MF in several or the most of channels, by minimum of average amplitude of the interference MF in all channels, or in other way. But the principal difference of proposed device is that it is common to all channels, unlike of other such systems, for example ENSS systems, manufactured separately for each channel.

In a further implementation of the device compensation is combined with another noise reduction methods, for example, with ENSS, electromagnetic shielding or with any other means. This is especially relevant when metering device—is sensitive magnetometer, which has a high resolution to MF, but at the same time low interference protection, especially unshielded areas with presence of high level industrial noise. In this case just proposed passive compensation is not enough, so it should be combined with other above-mentioned methods.

Proposed device is industrially applicable and could be easily manufactured, because it is made of industrially developed materials (copper, niobium or other metal wire, kaprolon, textolite, various fiber-reinforced plastics) and based on standard technological processes. Its application field—ultrasensitive biomagnetometry, including magnetocardiography, susceptometry or other branch, scientific biomedical research, low-temperature physics and technology.

The given embodiments of the device in the invention are described in detail only for the purpose of illustration. It is clear that in practice people experienced in the supersensitive biomagnetometry and/or cryogenic technology can make some changes and modifications in the design of the proposed device. However, we consider that if said modifications and changes are made without significant deviations from the essence and claims of proposed invention, they fall under this patent.

What is claimed is:

1. A device for compensating electromagnetic interferences during biomagnetic measurements at a high level of external electromagnetic interferences, comprising:
   a measuring device of biomagnetic signals,
   a device for passively compensating said electromagnetic interferences, wherein:
   the measuring device is configured to register three components of the biomagnetic signals, including three projections of the magnetic field vector and/or its spatial gradient of first or higher order,
   the device for compensating electromagnetic interferences comprises at least three compensation elements and a moving structure for moving the compensation elements, characterized in that, the compensation elements each comprise a short-circuited ring of arbitrary shape and are manufactured of electrically conductive materials with, the compensation elements are configured so that they have only inductive coupling with the said measuring device and no galvanic coupling, the compensation elements are placed around the said measuring device in space, and include three compensation elements placed in mutually intersecting planes respectively corresponding to said three projections, the moving structure comprises a shifting structure for shifting, a holding structure for holding, and a fixation structure for fixation of the compensation elements, the moving structure is configured to perform repeated displacement and fixation of the compensation elements for changing interference conditions at the location of the measuring device, said shifting, holding, and fixation structures are configured to are independently move the individual compensation elements, and, said fixation structures are configured to allow fixing of the compensation elements in positions with minimum amplitude of electromagnetic interferences at an the input of the said measuring device.

2. Device according to claim 1, characterized in that: the measuring device is placed within a cooler and cooled, using cryogenic liquids or any other means, and said compensation elements and moving structure are placed outside the cooler.

3. Device according to claim 2, characterized in that at least one compensation element is placed inside the cooler.

* * * * *